(12) United States Patent
Kim et al.

(10) Patent No.: US 11,660,047 B2
(45) Date of Patent: May 30, 2023

(54) CONSCIOUSNESS LEVEL DETERMINATION METHOD AND COMPUTER PROGRAM

(71) Applicant: BRAINU CO., LTD., Yongin-si (KR)

(72) Inventors: Kwang Moo Kim, Gyeonggi-do (KR); Seung Kyun Hong, Gwangmyeong-si (KR)

(73) Assignee: BRAINU CO., LTD., Yongin-si (KR)

( * ) Notice: Subject to any disclaimer, the term of this patent is extended or adjusted under 35 U.S.C. 154(b) by 146 days.

(21) Appl. No.: 17/123,786

(22) Filed: Dec. 16, 2020

(65) Prior Publication Data
US 2021/0369193 A1    Dec. 2, 2021

(30) Foreign Application Priority Data
May 27, 2020    (KR) .................. 10-2020-0063886

(51) Int. Cl.
*A61B 5/00*    (2006.01)
*G16H 40/67*    (2018.01)
(Continued)

(52) U.S. Cl.
CPC ............ *A61B 5/4821* (2013.01); *A61B 5/374* (2021.01); *A61B 5/397* (2021.01); *A61B 5/7203* (2013.01);
(Continued)

(58) Field of Classification Search
CPC .................................................. A61B 5/4821
(Continued)

(56) References Cited

U.S. PATENT DOCUMENTS 6,317,627 B1 *  11/2001  Ennen .................. A61B 5/4821
                                                         600/545
2007/0010755 A1   1/2007  Sarkela et al.
(Continued)

FOREIGN PATENT DOCUMENTS

| CN | 110680285 | 1/2020 |
| WO | 2012069887 | 5/2012 |
| WO | 2019179544 | 9/2019 |

OTHER PUBLICATIONS

Vahid Esmaeili et al., "Classifying Depth of Anesthesia Using EEG Features, a Comparison", 29th Annual International Conference of the IEEE EMBS, Lyon, France, Aug. 23-26, 2007, pp. 4106-4109.
(Continued)

*Primary Examiner* — Nicole F Lavert
(74) *Attorney, Agent, or Firm* — Kile Park Reed & Houtteman PLLC

(57) ABSTRACT

A step of extracting components of one or more frequency bands from a first section of an EEG; a step of calculating a first index for each of the components of one or more frequency bands, wherein the first index is calculated based on a degree to which a magnitude of each of the components of one or more frequency bands with respect to a magnitude of a predetermined reference component in the first section exceeds a predetermined threshold value; a step of calculating a probability value for each of one or more patient statuses from the first index for each of the components of one or more frequency bands using a trained artificial neural network; and a step of determining the consciousness level of the patient based on the probability value for each of the one or more calculated patient statuses.

16 Claims, 11 Drawing Sheets

(51) Int. Cl.
G16H 50/30 (2018.01)
A61B 5/397 (2021.01)
A61B 5/374 (2021.01)
G06N 3/08 (2023.01)
A61B 5/296 (2021.01)
A61B 5/398 (2021.01)
A61B 5/291 (2021.01)

(52) U.S. Cl.
CPC ............ *A61B 5/7267* (2013.01); *G06N 3/08* (2013.01); *G16H 40/67* (2018.01); *G16H 50/30* (2018.01); *A61B 5/291* (2021.01); *A61B 5/296* (2021.01); *A61B 5/398* (2021.01); *A61B 2562/063* (2013.01)

(58) Field of Classification Search
USPC .................................. 600/300–301
See application file for complete search history.

(56) References Cited

U.S. PATENT DOCUMENTS

| | | |
|---|---|---|
| 2010/0262377 A1 | 10/2010 | Jensen |
| 2015/0164413 A1 | 6/2015 | Wu et al. |
| 2017/0181693 A1* | 6/2017 | Kim .................... A61B 5/316 |
| 2018/0206784 A1 | 7/2018 | Jensen et al. |
| 2021/0007660 A1 | 1/2021 | Botero Rosas et al. |

OTHER PUBLICATIONS

Quan Liu et al., "A comparison of five different algorithms for EEG signal analysis in artifacts rejection for monitoring depth of anesthesia", Biomedical Signal Processing and Control, Mar. 2016, vol. 25, pp. 24-34.

Yue Gu et al., "Use of Multiple EEG Features and Artificial Neural Network to Monitor the Depth of Anesthesia", Sensors 2019, May 31, 2019.

International Search Report, corresponding to European Application No. 20212516.7 dated Jun. 21, 2022.

Written Opinion, corresponding to Singapore Application No. 10202012522U dated May 25, 2022.

* cited by examiner

CONSCIOUSNESS LEVEL DETERMINATION METHOD AND COMPUTER PROGRAM

BACKGROUND OF THE INVENTION

1. Field of the Invention

Embodiments of the present disclosure relate to a method and a computer program for determining the consciousness level of a subject using a trained artificial neural network.

2. Description of the Prior Art

In general, when a subject experiences pain in a medical practice such as surgery or treatment, the pain is eliminated or reduced by blocking nerve transmission through anesthesia. Depending on the patient's symptoms or a surgical site, general anesthesia may be performed, or partial anesthesia may be performed. In the case of general anesthesia, more detailed monitoring of the patient's condition is necessary because the patient cannot express his or her intention.

For this, it is necessary to continuously measure the depth of anesthesia during surgery. As a method of measuring the depth of anesthesia, a method of observing a clinical pattern and a method of analyzing a bioelectrical signal are used.

As the method of analyzing a bioelectrical signal, there is a method of measuring and analyzing an electroencephalogram (hereinafter, referred to as "EEG") in order to evaluate the effect of an anesthetic agent on the central nervous system, and conventional techniques measure and analyze the EEG in various ways.

Currently, the most widely used method of measuring the depth of anesthesia is a bispectral index (hereinafter, referred to as a "BIS") analysis method. The BIS analysis method is characterized in that the depth of anesthesia is quantified between 0 and 100.

In a depth of anesthesia measurement apparatus using the BIS analysis method, many problems have been reported about the accuracy in measuring the depth of anesthesia of a patient. There is a lot of difficulty in proving an algorithm error because the details of the analysis algorithm installed in the apparatus have not been disclosed.

In addition, the consciousness level measurement apparatus using the BIS analysis method has a problem in that the apparatus cannot accurately and quickly detect the anesthesia status of the patient because a tracking speed in tracking rapid changes in the anesthesia status is slow due to the characteristics of the scheme thereof.

SUMMARY OF THE INVENTION

1. Task to be Solved

The present disclosure was made to solve the above-described problems. The present disclosure provides an accurate measurement value of the depth of anesthesia even when an anesthesia condition changes and provides information on the depth of anesthesia in a timely manner even when there is a sudden change in anesthesia and consciousness.

In addition, the present disclosure provides information on the emotional status of a subject.

In addition, the present disclosure provides a depth of anesthesia for various subjects (e.g., animals other than humans).

2. Means to Solve the Problem

A method for determining a consciousness level of a patient according to an embodiment of the present disclosure may include: a step of extracting components of one or more frequency bands from a first section of an EEG; a step of calculating a first index for each of the components of one or more frequency bands, wherein the first index is calculated based on a degree to which a magnitude of each of the components of one or more frequency bands with respect to a magnitude of a predetermined reference component in the first section exceeds a predetermined threshold value; a step of calculating a probability value for each of one or more patient statuses from the first index for each of the components of one or more frequency bands using a trained artificial neural network; and a step of determining the consciousness level of the patient based on the probability value for each of the one or more calculated patient statuses.

The method of determining a consciousness of a patient according to an embodiment of the present disclosure may further include, before the step of extracting the components of one or more frequency bands, a step of acquiring an EEG of the patient, a step of generating the first section of the EEG including at least a part of the acquired EEG, and a step of removing noise from the first section of the EEG. In this case, in the step of extracting the components of one or more frequency bands, the components of one or more frequency bands may be extracted from the first section of the EEG, from which the noise has been removed.

In the step of acquiring the EEG, the EEG of the patent sampled at a predetermined sampling frequency may be acquired.

In the step of generating the first section of the EEG, the first section of the EEG may be generated such that the EEG within a predetermined time interval from a time point of determining the consciousness level is included therein.

The step of removing the noise may include a step of replacing a first partial section including a time point at which the magnitude of the EEG exceeds a predetermined threshold magnitude within the first section of the EEG with a second partial section different from the first partial section, wherein the first partial section and the second partial section may be at least a part of the first section.

The step of removing the noise may include a step of replacing the first section of the EEG with a second section of the EEG when a pattern, in which the magnitude of the EEG within the first section of the EEG exceeds the predetermined threshold magnitude, corresponds to a preset pattern, wherein the second section is different from the first section and may be at least a part of the EEG.

In the step of extracting, a first component of 0.5 to 4 Hz, a second component of 4 to 8 Hz, a third component of 8 Hz to 16 Hz, a fourth component of 16 to 25 Hz, a fifth component of 25 to 30 Hz, a sixth component of 30 to 48 Hz, and a reference component of 0.5 to 55 Hz may be extracted from the first section of the EEG.

The components of one or more frequency bands may include a magnitude of a component of each of the frequency bands at one or more time point belonging to the first section, and the step of calculating the first index may include a step of calculating the magnitudes of the components of one or more frequency bands with respect to a magnitude of the reference component for each of the one or more time points, a step of determining a time point at which the calculated magnitudes exceed the predetermined threshold value as an excess time point, and a step of calculating the first index based on a ratio of a number of excess time points to a total number of time points belonging to the first section. The predetermined threshold value may be determined based on an absolute magnitude of the reference component within the first section.

The method of measuring a consciousness level according to an embodiment of the present disclosure may further include, before the step of calculating the probability value, a step of generating input data of the artificial neural network using a combination of first indices for each of the components of one or more frequency bands.

In the method of measuring a consciousness level according to an embodiment of the present disclosure, a first index for each of N frequency bands (N is a natural number) is calculated from the first section of the patient's first EEG acquired through a first channel, and a first index for each of the N frequency bands is calculated from a first section of the patient's second EEG acquired through a second channel distinguished from the first channel, and the step of generating the input data may include a step of generating $N^2$ pieces of first input data based on a combination of the N first indices for the first channel and the N second indices for the second channel, a step of generating N pieces of second input data corresponding to the N first indices for the first channel, a step of generating N pieces of third input data corresponding to the N first indices for the second channel, a step of generating M pieces of fourth input data (M is a natural number) based on an EMG signal, and a step of generating the input data including the first input data, the second input data, the third input data, and the fourth input data. In this case, the N may be 6, and the M may be 1.

The artificial neural network may be a neural network that includes data on which an EEG characteristic has been reflected and data on which an EMG characteristic has been reflected, and that has learned the correlations between the EEG characteristic, the EMG characteristic, and the patient status based on training data labeled with the patient status data corresponding to the EEG characteristic and the EMG characteristic. The data on which the EEG characteristic has been reflected may include $N^2$ pieces of first data based on a combination of N first indices (N is a natural number) for an EEG acquired through a first channel and N first indices for an EEG acquired through the second channel, N pieces of second data corresponding to the N first indices for the first channel, N pieces of third data corresponding to the N first indices for the second channel, and M pieces of fourth data (M is a natural number) based on the EMG signal. The patient status data may include a probability that the patient corresponds to each of K patient statuses (K is a natural number).

The step of determining the consciousness level may include a step of calculating a normalized probability value by normalizing a probability value for each of the one or more patient statuses, a step of applying a weight set corresponding to a patient status having a largest probability value among normalized probability values to the normalized probability values, and a step of determining the consciousness level based on a sum of weighted normalized probability values.

The one or more patient statuses may include an awake status, a sedation status, a general anesthesia status, a deep anesthesia status, and a brain death status, and in the step of applying the weight set, any one of weight sets for each of the five patient statuses is applied to the normalized probability values.

In the step of determining the consciousness level based on the sum of the weighted normalized probability values, the consciousness level may be determined based on a first consciousness level obtained by applying a predetermined first weight to the sum of the weighted normalized probability values and a consciousness level obtained by applying a second weight value to a second consciousness level determined through a second method.

3. Effects of the Invention

According to the present disclosure, it is possible to more accurately measure the depth of anesthesia or the status of consciousness of a patient.

In particular, by improving the problem of low response speed when the degree of anesthesia changes rapidly due to a slow tracking speed, which is a problem of the conventional BIS analysis method based on a depth of anesthesia measurement apparatus, the depth of anesthesia measurement apparatus of the present disclosure is capable of responding more quickly than the conventional depth of anesthesia measurement apparatus when changing from awake status to a hypnosis status, so that a patient status can be determined accurately and in a timely manner.

In addition, since the present disclosure facilitates real-time processing due to the simplicity of algorithm, it is possible to more accurately capture a status change during anesthesia.

In addition, the present disclosure is capable of providing information on an emotional state of a subject.

In addition, the present disclosure can provide depth of anesthesia for various subjects (e.g., animals other than humans).

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION OF THE EXEMPLARY EMBODIMENTS

Figure 1:
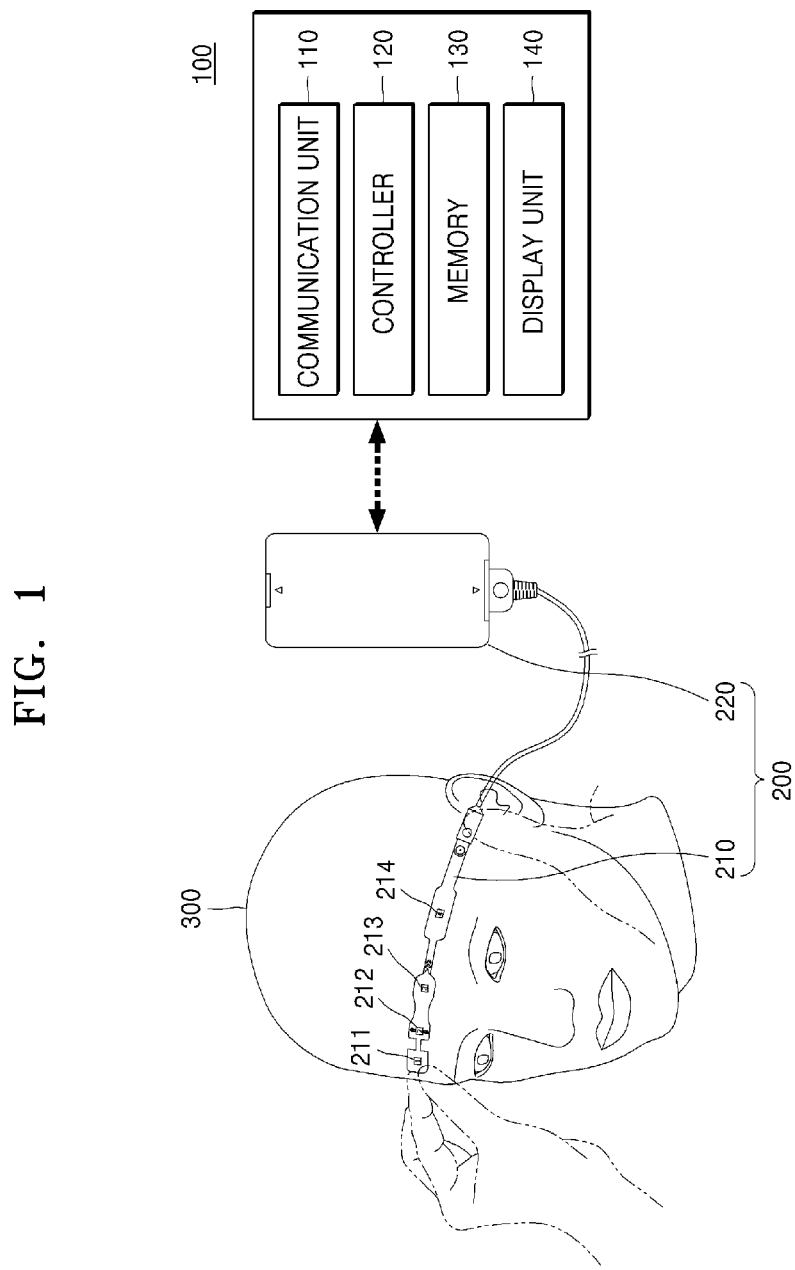
FIG. 1 is a view schematically illustrating the configuration of a consciousness level determination system according to an embodiment of the present disclosure.

The present disclosure may be variously modified and may have various embodiments. Thus, specific embodiments are illustrated in the drawings, and are described in detail in the detailed description. The effects and features of the present disclosure and the way of attaining them will become apparent with reference to the embodiments described below in detail in conjunction with the accompanying drawings. However, the present disclosure is not limited to the embodiments described below, and may be implemented in various forms.

Hereinafter, the embodiments of the present disclosure will be described in detail with reference to the accompanying drawings, and in the following description made with reference to the drawings, the same or similar elements will be denoted by the same reference numerals, and redundant descriptions thereof will be omitted.

In the following embodiments, terms, such as "first" and "second" are not used in limited meaning, but are used to distinguish one element from another element. In the following embodiments, singular expressions include plural expressions unless the context clearly indicates otherwise. In the following embodiments, terms, such as "including" and "having", specify the presence of features or components described in this specification, but do not preclude in advance the presence or addition of one or more other features or components. For convenience of description, components may be exaggerated or reduced in magnitude in the drawings. For example, the magnitude and shapes of each component illustrated in the drawings are arbitrarily shown for convenience of description, and thus the present disclosure is not necessarily limited to those illustrated in the drawings.

FIG. 1 is a view schematically illustrating the configuration of a consciousness level determination system according to an embodiment of the present disclosure.

A consciousness level determination system according to an embodiment of the present disclosure may determine the level of consciousness of a patient 300 based on a biosignal of the patient 300. At this time, the term "biological signal" refers to various types of signals measured directly or indirectly from the body of the patient 300, such as an EEG signal of the patient 300, an electromyogram (hereinafter, referred to as "EMG") signal of the patient 300, and an electrooculogram (hereinafter, referred to as "EOG") signal of the patient 300. In addition, the term "consciousness level" refers to a degree to which the patient 300 normally recognizes and distinguishes between himself/herself and the surrounding environment, and may mean a degree to which the patient 300 can be awakened upon a specific stimulus. In the present description, the "depth of anesthesia" may sometimes be used as an index indicating the consciousness level, but this is illustrative and the spirit of the present disclosure is not limited thereto. For example, as an index indicating the consciousness level, the emotional status and the sleep state of the patient 300 may be used in addition to the depth of anesthesia.

Meanwhile, although the patient 300 is illustrated as an example of a subject in FIG. 1, the spirit of the present disclosure is not limited thereto. Therefore, as illustrated in FIG. 1, the object may be a patient 300, that is, a human, or may be a target animal.

The consciousness level determination system according to an embodiment of the present disclosure may include a user terminal 100 and a consciousness level determination apparatus 200, as illustrated in FIG. 1.

The consciousness level determination apparatus 200 according to an embodiment of the present disclosure includes a sensing unit 210 attached to the body of a patient 300 and configured to acquire a biosignal of the patient 300, and a signal processor 220 configured to process a biosignal of the patient 300 acquired by the sensing unit 210 and to transmit the biosignal to the user terminal 100.

The sensing unit 210 according to an embodiment of the present disclosure may mean a means attached to the body of the patient 300 to obtain a biosignal of the patient 300 as described above. In this case, the sensing unit 210 may include a reference electrode 211 configured to set a reference potential, a ground electrode 212 configured to set a ground potential, a first channel electrode 213 configured to measure an EEG and an EMG signal, and a second channel electrode 214 configured to measure an EEG, as illustrated in FIG. 1.

Each of the plurality of electrodes 211, 212, 213, 214 can be attached to the scalp of the patient 300 in a non-invasive or invasive manner so as to acquire a biosignal when the sensing unit 210 is worn on the head of the patient 300.

Meanwhile, the shape of the sensing unit 210 illustrated in FIG. 1, the number of electrodes 211, 212, 213, and 214 included in the sensing unit 210, and the arrangement of electrodes 211, 212, 213, and 214 are illustrative, and the spirit of the present disclosure is not limited thereto. Therefore, any means may correspond to the sensing unit 210 of the present disclosure, as long as the means can be attached to the body of the patient 300 so as to acquire a biosignal of the patient 300.

The sensing unit 210 according to another embodiment of the present disclosure may be configured by omitting any one of the reference electrode 211 and the ground electrode 212 described above. In other words, the sensing unit 210 according to another embodiment of the present disclosure may be configured to include the reference electrode 211, the first channel electrode 213, and the second channel electrode 214, or may be configured to include the ground electrode 212, the first channel electrode 213, and the second channel electrode 214. In this case, the reference potential and the ground potential correspond to the same potential, and may be set by the reference electrode 211 or the ground electrode 212.

The signal processor 220 according to an embodiment of the present disclosure may mean a means for processing a biosignal acquired by the sensing unit 210 and transmitting the biosignal to the user terminal 100. In this case, "processing" a signal means processing a signal in the form that can be calculated by the user terminal 100, and may mean, for example, sampling or amplifying a signal.

The signal processor 220 according to an embodiment of the present disclosure may amplify a biosignal acquired by the sensing unit 210. In addition, the signal processor 220 according to an embodiment of the present disclosure may sample the biosignal acquired by the sensing unit 210 at a predetermined sampling frequency.

For example, the signal processor 220 may amplify an EEG acquired from each of the first channel electrode 213 and the second channel electrode 214 of the sensing unit 210 at a predetermined ratio and may then sample the EEG at a sampling frequency of 250 Hz.

Similarly, the signal processor 220 may amplify an EMG signal acquired from the first channel electrode 213 of the sensing unit 210 at a predetermined rate and may then sample the EMG signal at a sampling frequency of 250 Hz.

The signal processor 220 according to an embodiment of the present disclosure may transmit biosignals amplified and sampled according to the above-described processes to a user terminal 100 through various communication methods. For example, the signal processor 220 may transmit a biosignal (amplified and sampled) to the user terminal 100 through a Bluetooth communication method, or may transmit a biosignal to the user terminal 100 through a Wi-Fi communication method. Of course, the signal processor 220 may transmit a biosignal to the user terminal 100 using various known wired communication methods.

The user terminal 100 according to an embodiment of the present disclosure may measure the depth of anesthesia of the patient 300 based on biosignals (e.g., amplified and sampled signals such as an EEG, an EMG signal, and an EOG signal acquired from each, for example, two channels) transmitted by the signal processor 220.

In this case, the user terminal 100 may be a general-purpose electronic device in which an application for measuring the depth of anesthesia is installed. For example, the user terminal 100 may be a mobile phone (or a tablet PC) in which an application for measuring the depth of anesthesia is installed. In addition, the user terminal 100 may be a dedicated electronic device, in which an application for measuring the depth of anesthesia runs.

The user terminal 100 according to an embodiment of the present disclosure may include a communication unit 110, a controller 120, a memory 130, and a display unit 140, as illustrated in FIG. 1. In addition, although not illustrated in the drawing, the user terminal 100 according to the present embodiment may further include an input/output unit, a program storage unit, or the like.

The communication unit 110 according to an embodiment of the present disclosure may include hardware and software that are necessary for the user terminal 100 to transmit and receive signals such as control signals or data signals through wired or wireless connection with other devices such as the signal processor 220. For example, the communication unit 110 may include hardware and software for transmitting and receiving data to and from the signal processor 220 in a Bluetooth method. Meanwhile, when the user terminal 100 is a general-purpose electronic device, the communication unit 110 may further include a communication modem and software for transmitting and receiving data using a general-purpose communication network (e.g., an LTE communication network, a 3G communication network, or a Wi-Fi communication network).

The controller 120 according to an embodiment of the present disclosure may include all kinds of devices capable of processing data, such as a processor. Here, the "processor" may refer to a data processor embedded in hardware having, for example, a circuit physically structured to perform a function represented by codes or instructions included in a program. Examples of data processors embedded in hardware as described above may include processors, such as a microprocessor, a central processing unit (CPU), a processor core, a multiprocessor, and an application-specific integrated device (ASIC), and a field programmable gate array (FPGA), but the scope of the present disclosure is not limited thereto.

The memory 130 according to an embodiment of the present disclosure performs a function of temporarily or permanently storing data processed by the user terminal 100. The memory may include a magnetic storage medium or a flash storage medium, but the scope of the present disclosure is not limited thereto. For example, the memory 130 may temporarily and/or permanently store a biosignal received from the signal processor 220. Also, the memory 130 may temporarily and/or permanently store weights constituting a trained artificial neural network.

The display unit 140 according to an embodiment of the present disclosure may perform a function of providing the measured depth of anesthesia to the user. The display unit 140 may be implemented with various known display devices such as an LCD, an OLED, and a micro-LED. However, this is illustrative, and a device for displaying a screen according to an electrical control signal may correspond to the display unit 140 of the present disclosure.

Hereinafter, the method of measuring the depth of anesthesia of a patient by the controller 120 of the user terminal 100 will be described.

The controller 120 according to an embodiment of the present disclosure may acquire a biosignal of the patient 300.

The controller 120 according to an embodiment of the present disclosure may acquire an EEG of the patient 300. For example, the controller 120 may acquire an EEG by receiving the EEG from the signal processor 220 described above. The EEG acquired at this time may be an EEG amplified and sampled at a predetermined sampling frequency. In addition, the controller 120 may acquire two EEGs acquired through different channels from the signal processor 220.

Meanwhile, the controller 120 according to an embodiment of the present disclosure may further acquire an EMG signal along with an EEG. Of course, the EMG signal acquired at this time may also be an EMG signal amplified and sampled at a predetermined sampling frequency.

The controller 120 according to an embodiment of the present disclosure may acquire a biosignal of the patient 300 in real time. In this case, the controller 120 may temporarily and/or permanently store the past biosignals in the memory 130 and may use the biosignals for measuring the depth of anesthesia of the patient.

The controller 120 according to an embodiment of the present disclosure may generate a first section of an EEG including at least a part of the acquired EEG.

Figure 2:
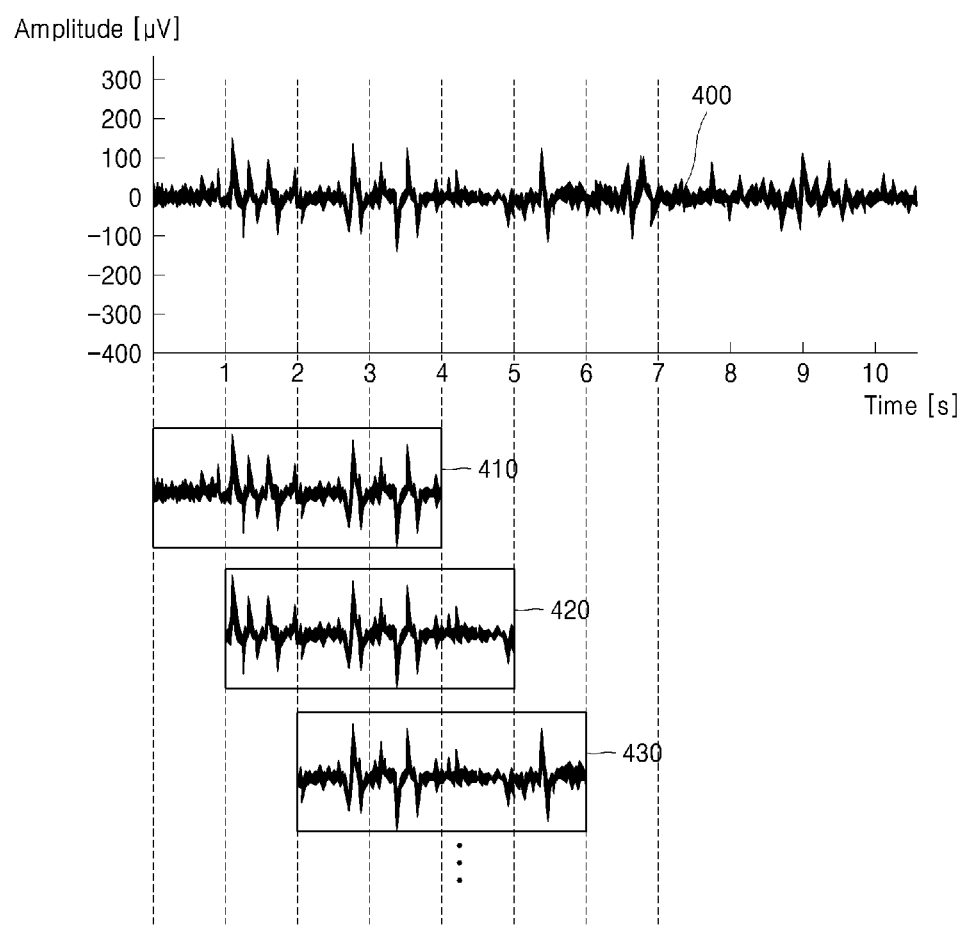
FIG. 2 is a view for describing a method in which the controller 120 according to an embodiment of the present disclosure generates a first section of an EEG 400.

FIG. 2 is a view for describing a method in which the controller 120 according to an embodiment of the present disclosure generates a first section of an EEG 400.

Hereinafter, for convenience of description, the EEG 400 of the patient 300 is generated as shown in the drawing, and the current time points are assumed to be 4 seconds, 5 seconds, and 6 seconds, respectively.

In generating the first section of the EEG 400, the controller 120 according to an embodiment of the present disclosure may generate a first section to include therein a past EEG within a predetermined time interval from the time point for determining the depth of anesthesia (i.e., the current time point).

For example, when it is assumed that the current time point at which the depth of anesthesia is determined is 4 seconds, the controller 120 may generate a first section 410 of a EEG including a past EEG within a predetermined time interval (assumed as 4 seconds) from the current time point (4 seconds). Similarly, when the current time point is 5 seconds, the controller 120 may generate a first section 420 of the EEG, and when the current time point is 6 seconds, the controller 120 may generate a first section 430 of the EEG.

In this case, the "predetermined time interval" may be variously set depending on system characteristics. For example, in a system requiring a quick response, a predetermined time interval may be set to be relatively short. For example, in a system requiring a correct response, a predetermined time interval may be set to be relatively long.

The controller 120 according to an embodiment of the present disclosure may generate the first section for each of two EEGs acquired through different channels according to the above-described processes. In addition, the controller 120 according to an embodiment of the present disclosure may repeatedly generate the first section based on the current time point depending on the passage of time (i.e., depending on the change of the time point for determining the depth of anesthesia).

The controller 120 according to an embodiment of the present disclosure may remove noise in the first section of the EEG generated according to the above-described processes.

Figure 3:
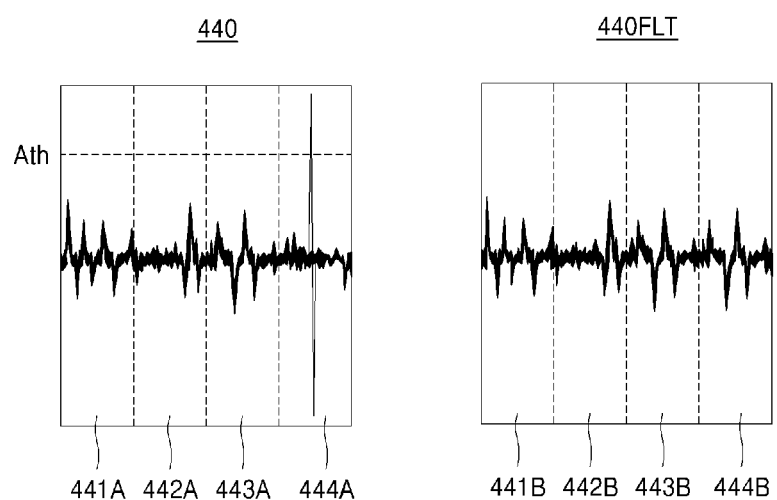
FIG. 3 is a view for describing a method in which the controller 120 according to an embodiment of the present disclosure removes noise from the first section 440 of an exemplary EEG and generates a first section 440FLT of the EEG, from which noise has been removed.

FIG. 3 is a view for describing a method in which the controller 120 according to an embodiment of the present disclosure removes noise from the first section 440 of an exemplary EEG and generates a first section 440FLT of the EEG, from which noise has been removed.

The controller 120 according to an embodiment of the present disclosure may replace a first partial section 444A having a magnitude exceeding a predetermined threshold magnitude Ath with a second partial section 443A different from the first partial section within the first section 440 of the EEG.

In this case, when the magnitude of the EEG at any one time point within the first partial section 444A exceeds the predetermined threshold magnitude Ath, the controller 120 may determine that the magnitude of the EEG within the corresponding section 444A exceeds the predetermined threshold magnitude Ath. In addition, the controller 120 may replace the corresponding section 444A using the section 443A adjacent to the section 444A.

Accordingly, the controller 120 may generate a first section 440FLT of an EEG, from which noise has been removed, and which has first to third partial sections 441B, 442B, and 443B, which are respectively the same as the first to fourth partial sections 441A, 442A, and 443A of the first section 440, and a fourth partial section 444B, which is the same as the third partial section 443A of the first section 440.

However, the length and the threshold magnitude Ath of the partial sections, and the method of replacing the partial sections are illustrative, and the spirit of the present disclosure is not limited thereto.

In an optional embodiment, when a pattern, in which the magnitude of the EEG within the first section 440 of the EEG exceeds the predetermined threshold magnitude, corresponds to a preset pattern, the controller 120 may replace the first section 440 of the EEG with the second section of the EEG. In this case, the second section of the EEG is a section different from the first section 440 of the EEG, and may be, for example, an EEG of a section adjacent to the first section.

In addition, the "preset pattern" may be variously set depending on the purpose of the system. For example, the preset pattern may be a pattern in which an EEG having a magnitude exceeding a predetermined threshold magnitude is generated in a plurality of partial sections within the same section, or a pattern in which an EEG having a magnitude exceeding a predetermined threshold magnitude is generated in two or more successive partial sections. However, such a pattern is illustrative, and the spirit of the present disclosure is not limited thereto.

The controller 120 according to an embodiment of the present disclosure may extract components of one or more frequency bands from the first section of the EEG generated according to the above-described processes (or the first section of an EEG, from which noise has been removed).

Figure 4:
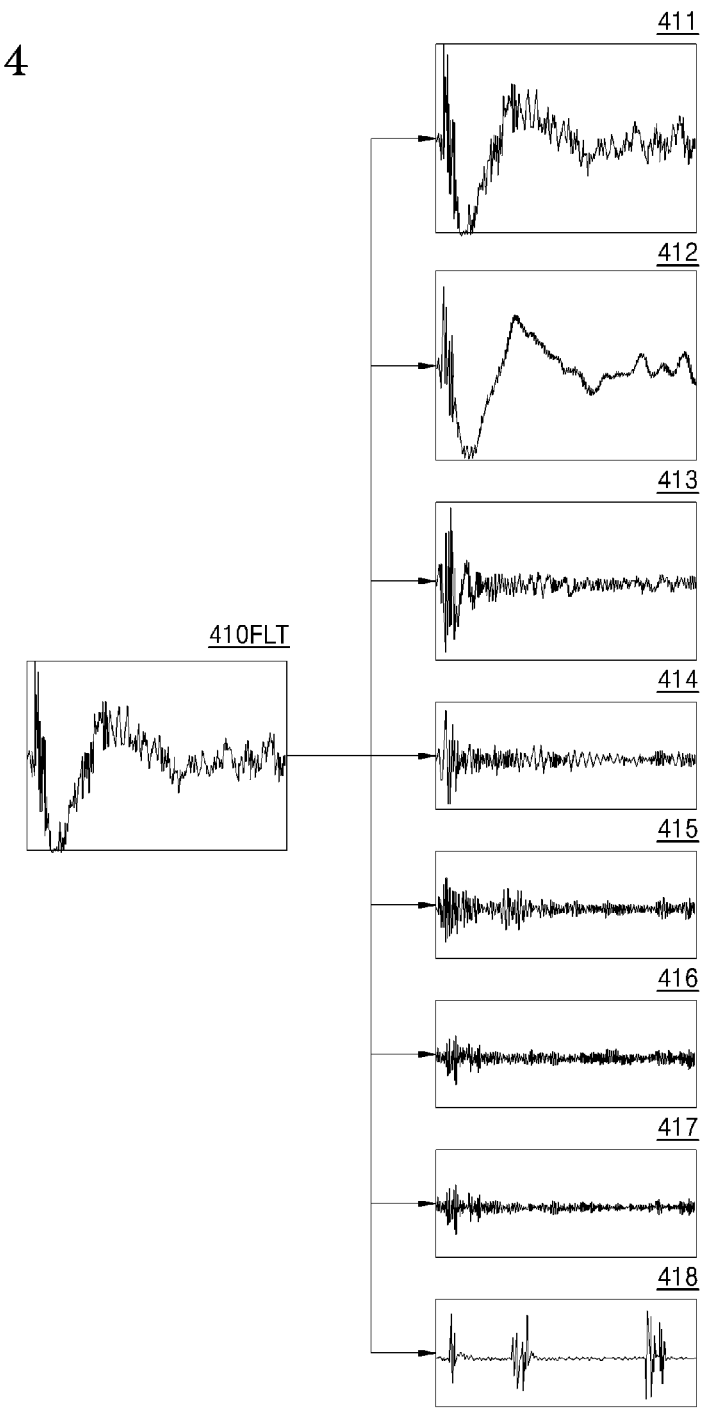
FIG. 4 is a view for describing a process in which the controller 120 according to an embodiment of the present disclosure extracts components 411, 412, 413, 414, 415, 416, 417, and 418 of one or more frequency bands from a first section 410FLT of an EEG, from which noise has been removed.

FIG. 4 is a view for describing a process in which the controller 120 according to an embodiment of the present disclosure extracts components 411, 412, 413, 414, 415, 416, 417, and 418 of one or more frequency bands from a first section 410FLT of an EEG, from which noise has been removed.

The controller 120 according to an embodiment of the present disclosure may extract a first component 412 of 0.5 to 4 Hz, a second component 413 of 4 to 8 Hz, a third component 414 of 8 Hz to 16 Hz, a fourth component 415 of 16 to 25 Hz, a fifth component 416 of 25 to 30 Hz, a sixth component 417 of 30 to 48 Hz, a reference component 411 of 0.5 to 55 Hz, and a BSR component 418 of 0.5 to 30 Hz, from the first section 410FLT of an EEG, from which noise has been removed.

The controller 120 according to an embodiment of the present disclosure may extract components 411, 412, 413, 414, 415, 416, 417, and 418 of one or more frequency bands from the first section 410FLT of the EEG, from which noise has been removed using frequency filters that correspond to the one or more frequency bands, respectively. For example, the controller 120 may extract the first component 412 using a band-pass filter having a pass band of 0.5 to 4 Hz.

The extracted components 411, 412, 413, 414, 415, 416, 417, and 418 of one or more frequency bands may have the same length of time as the first section 410FLT of the EEG, from which noise has been removed. In addition, the components 411, 412, 413, 414, 415, 416, 417, and 418 of one or more frequency bands may include a magnitude of a component of each frequency band at one or more time points belonging to the first section.

For example, when the sampling frequency of the signal processor 220 is 250 Hz and the length of the first section 410FLT of the EEG, from which noise has been removed, is 4 seconds, 1000 time points (or 1000 sampling time points) and the magnitude of the EEG at each time point may be included within the first section 410FLT of the EEG, from which noise has been removed. Accordingly, the components 411, 412, 413, 414, 415, 416, 417, and 418 of one or more frequency bands may also include the magnitude of the component of each frequency band at each of 1000 time points belonging to the first section.

In other words, the components 411, 412, 413, 414, 415, 416, 417, and 418 of one or more frequency bands may also include the magnitude of the component of each frequency band at each of 1000 time points belonging to the first section.

The controller 120 according to an embodiment of the present disclosure may calculate a first index for each of the components 411, 412, 413, 414, 415, 416, 417, and 418 of one or more frequency bands.

Figure 5:
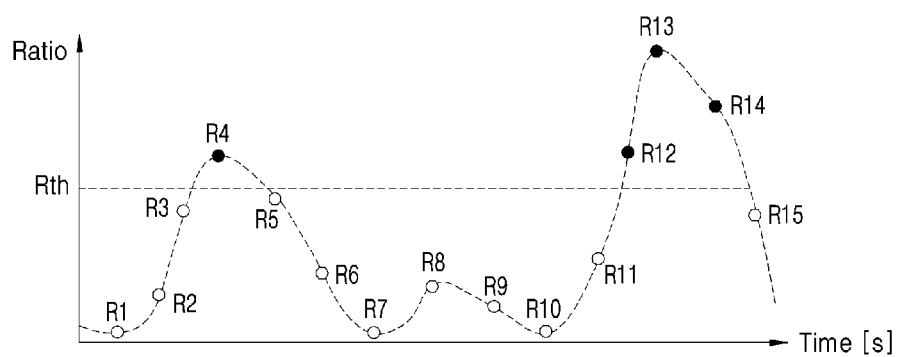
FIG. 5 is a view for describing a method in which the controller 120 according to an embodiment of the present disclosure calculates a first index.

FIG. 5 is a view for describing a method of calculating a first index using the controller 120 according to an embodiment of the present disclosure. For convenience of description, it is assumed that the graph represented in FIG. 5 relates to a first component, and 15 time points are included in the first section for the first component.

The controller 120 according to an embodiment of the present disclosure may calculate a first index based on the extent to which the magnitude of each of the components of one or more frequency bands exceeds a predetermined threshold value Rth with respect to the magnitude of a predetermined reference component in the first section. For example, the controller 120 according to an embodiment of the present disclosure may calculate the magnitude of each of the components of one or more frequency bands with respect to the magnitude of the reference component for each of one or more time points (i.e., 15 time points) belonging to the first section.

In this case, the reference component may be the reference component 411 extracted according to the process described with reference to FIG. 4, and the components of one or more frequency bands may be the components 412 to 417 extracted according to the process described with reference to FIG. 4. For example, the controller 120 may calculate the ratio R1 of the magnitude of the first component 412 at the first time point of the first section to the magnitude of the reference component 411 at the first time point of the first section. Similarly, the controller may calculate the ratios (R2 to R15) of the magnitude of the first component 412 to the magnitudes of the reference component 411 at the remaining time points. Of course, the controller 120 may calculate the ratio at each of the plurality of time points according to the above-described process for each of the remaining components 413 to 417.

The controller 120 according to an embodiment of the present disclosure may determine a time point at which the magnitude of the calculated ratio exceeds a predetermined threshold value Rth, as an excess time point. For example, the controller 120 may determine a time point corresponding to each of R4, R12, R13, and R14 of FIG. 5 as an excess time point. Of course, the controller may determine the excess time points for the remaining components 413 to 417 according to the same process.

The controller 120 according to an embodiment of the present disclosure may calculate a first index based on a ratio of the number of excess points to the total number of time points belonging to the first section. For example, for the first component 412, the controller 120 may calculate the first index as 4/15 using 15 that is the total number of time points and 4 that is the number of excess time points. In this case, the controller 120 may normalize the first index by multiplying a predetermined value by the calculated first index. Of course, the controller may calculate the first index for each of the remaining components 413 to 417 according to the same process.

Meanwhile, the controller 120 according to an embodiment of the present disclosure may determine a predetermined threshold value Rth based on the absolute magnitude of the reference component within the first section. Since the reference component is extracted from a wide frequency band, when the magnitude of the EEG in the first section is large, the predetermined threshold value Rth may be determined relatively high, and when the magnitude of the EEG is small, the predetermined threshold value Rth may be determined relatively low.

The controller 120 according to an embodiment of the present disclosure may calculate the first index for each of two EEGs acquired through different channels according to the above-described processes. In addition, the controller 120 according to an embodiment of the present disclosure may repeatedly calculate the first indexes for the updated first section according to the update of the first section.

The controller 120 according to an embodiment of the present disclosure may calculate a second index that reflects the degree to which an EEG in the first section conforms to a predetermined pattern.

Figure 6:
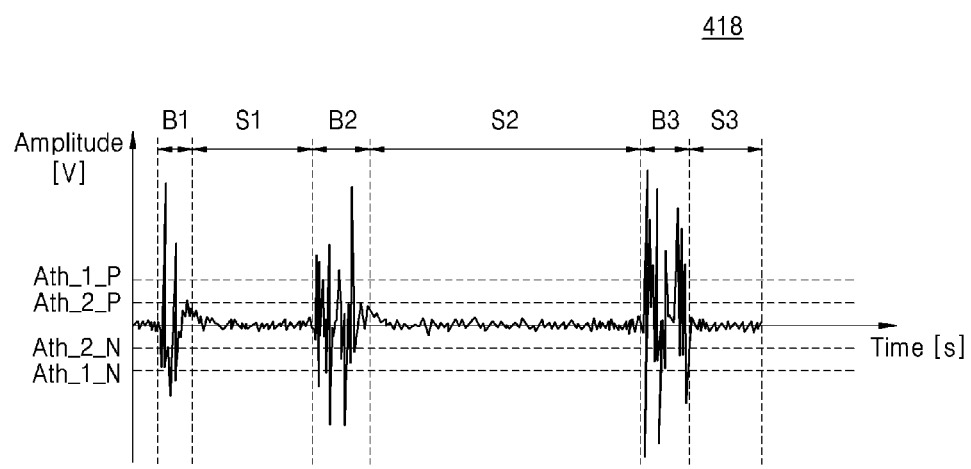
FIG. 6 is a view for describing a method in which the controller 120 according to an embodiment of the present disclosure calculates a second index.

FIG. 6 is a view for describing a method in which the controller 120 according to an embodiment of the present disclosure calculates a second index.

The controller 120 according to an embodiment of the present disclosure may calculate a second index from a BSR component 418 extracted from the first section 410FLT of the EEG, from which noise has been removed according to the process described with reference to FIG. 4. In this case, the BSR component 418 may be obtained by extracting a component of 0.5 to 30 Hz from the first section 410FLT of the EEG, from which noise has been removed.

The controller 120 according to an embodiment of the present disclosure may identify the number of repetitions of a first type signal (or a burst type signal) and a second type signal (or a suppression type signal) in the BSR component 418. The first type signal is of a type in which an EEG having a magnitude (i.e., the absolute value of the amplitude of the signal) greater than or equal to the first threshold magnitude occurs during a first duration, and the second type signal is of a type in which an EEG having a magnitude less than or equal to the second threshold magnitude occurs during a second duration. In this case, the first duration may be shorter than the second duration.

In FIG. 6, the first type signal is of a type in which an EEG having a magnitude greater than or equal to a first threshold magnitude (Ath_1_P or Ath_1_N) occurs during the first duration shorter than the second duration, and the second type signal is of a type in which an EEG having a magnitude less than or equal to a second threshold magnitude (Ath_2_P or Ath_2_N) occurs during the second duration longer than the first duration. In this case, the first threshold magnitude (Ath_1_P or Ath_1_N) and the second threshold magnitude (Ath_2_P or Ath_2_N) may be preset to an appropriate magnitude.

Therefore, in FIGS. 6, B1, B2, and B3 may each correspond to the first type signal, and S1, S2, and S3 may each correspond to the second type signal.

Meanwhile, in FIG. 6, the controller 120 according to an embodiment of the present disclosure may identify (or determine) the number of repetitions of the first type signal and the second type signal as 3.

The controller 120 according to an embodiment of the present disclosure may calculate a second index based on a ratio of the number of repetitions of a signal to a value corresponding to the length of the first section 410FLT of an EEG. In this case, the value corresponding to the length of the first section 410FLT of the EEG may be a value proportional to the number of time points (e.g., 1000) included in the first section 410FLT of the EEG. Accordingly, the controller 120 may determine the second index from the BSR component 418 of FIG. 4 as 3/1000 or a value proportional to 3/1000.

Meanwhile, the method described with reference to FIG. 6 is an exemplary method for determining how much the EEG of the first section 410FLT conforms to a predetermined pattern, and the spirit of the present disclosure is not limited thereto. Any method capable of determining whether or not a signal of a specific unit pattern is repeated in the EEG of the first section 410FLT and the number of repetitions may be used without limitation to calculate the second index in the present disclosure.

The controller 120 according to an embodiment of the present disclosure may calculate a third index based on at least one biosignal corresponding to a patient status. For example, the controller 120 according to an embodiment of the present disclosure may generate a third index based on an EMG signal measured by the first channel electrode 213 of the sensing unit 210.

However, using the EMG signal as an element for generating the third index as described above is illustrative, and the method of calculating the third index may vary depending on the configuration of the consciousness level determination system. For example, when the consciousness level determination system further includes a component for measuring other biological signals of the patient 300, the controller 120 may generate the third index based on the signal measured by the component.

In an optional embodiment, the controller 120 may generate the third index based on the patient's EOG signal.

The controller 120 according to an embodiment of the present disclosure may determine the depth of anesthesia of the patient 300 based on at least one of the first index, the second index, and the third index calculated according to the above-described processes.

The controller 120 according to an embodiment of the present disclosure may determine the depth of anesthesia of the patient 300 using the trained artificial neural network and the first index for each of the components of one or more frequency bands and the third index based on the EMG signal.

In the present disclosure, the "artificial neural network" may be a neural network that includes data on which EEG characteristics have been reflected and data on which EMG characteristics have been reflected, and that has learned the correlations between the EEG characteristics, the EMG characteristics, and the patient status based on the training data labeled with the patient status data corresponding to the EEG characteristics and the EMG characteristics.

In other words, the artificial neural network may be a neural network that has been trained to output the patient status data in response to input of data on which the EEG characteristics have been reflected and data on which the EMG characteristics have been reflected.

In the present disclosure, the artificial neural network may be implemented as a neural network model of various structures. For example, the artificial neural network may be implemented as a CNN model, an RNN model, or an LSTM model. However, these neural network models are examples, and a means capable of learning the correlation between input and output based on training data can be used as the artificial neural network of the present disclosure.

Figure 7:
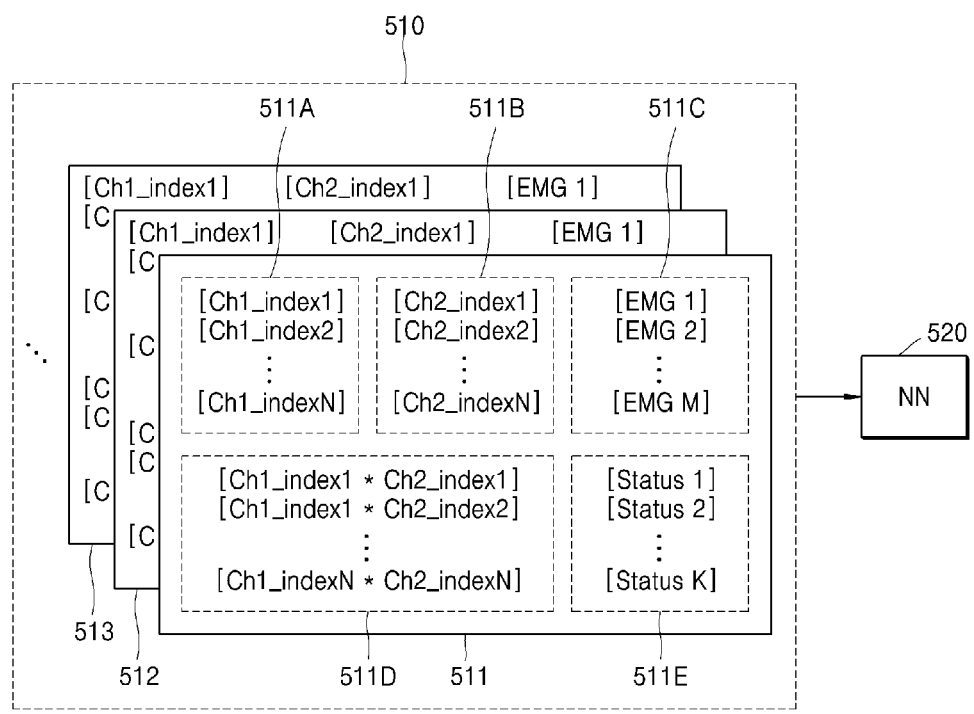
FIG. 7 is a view for describing a process in which the controller 120 according to an embodiment of the present disclosure trains an artificial neural network 520 using multiple pieces of training data 510.

FIG. 7 is a view for describing a process in which the controller 120 according to an embodiment of the present disclosure trains an artificial neural network 520 using multiple pieces of training data 510.

As described above, the artificial neural network 520 may be a neural network that has learned the correlations between the EEG characteristics, the EMG characteristics, and a patient status based on multiple pieces of training data 510.

In this case, each of multiple pieces of training data 510 may include data in which the EEG characteristics have been reflected and data on which the EMG characteristics have been reflected, as described above, and may be data labeled with patient status data corresponding to the EEG characteristics and the EMG characteristics.

For example, first training data 511 may, as data on which EEG characteristics have been reflected include, N pieces of data 511A (N is a natural number) corresponding to first indices for each of N frequency bands calculated from the first section of a first EEG (acquired through the first channel) of a patient 300, N pieces of data 511B corresponding to first indices for each of N frequency bands calculated from the first section of a second EEG (acquired through the second channel) of the patient 300, and $N^2$ pieces of data 511D generated based on a combination of N first indices 511A for the first channel and N first indices 511B for the second channel.

In addition, the first training data 511 may include M pieces of data 511C (M is a natural number) based on an EMG signal, as data on which the EMG characteristics have been reflected.

In addition, the first training data 511 may be labeled with patient state data 511E including a probability that the corresponding patient 300 corresponds to each of K patient statuses. In this case, for example, N may be 6, M may be 1, and K may be 5.

Remaining training data including a second training data 512 and a third training data 513 may also include the same data as the first training data 511, and may be labeled with the same data. A specific method of generating individual data included in individual training data will be described later with reference to FIG. 8.

As described above, the present disclosure may train the artificial neural network 520 based on data generated from a patient's biosignal and training data including a probability that the patient corresponds to each of multiple patient statuses. Accordingly, the artificial neural network 520 may output a probability that the corresponding patient corresponds to each of the multiple patient statuses according to the input of data generated from the patient status signals. Hereinafter, it is assumed that the artificial neural network 520 has been trained based on multiple pieces of training data 510 described with reference to FIG. 7.

Figure 8:
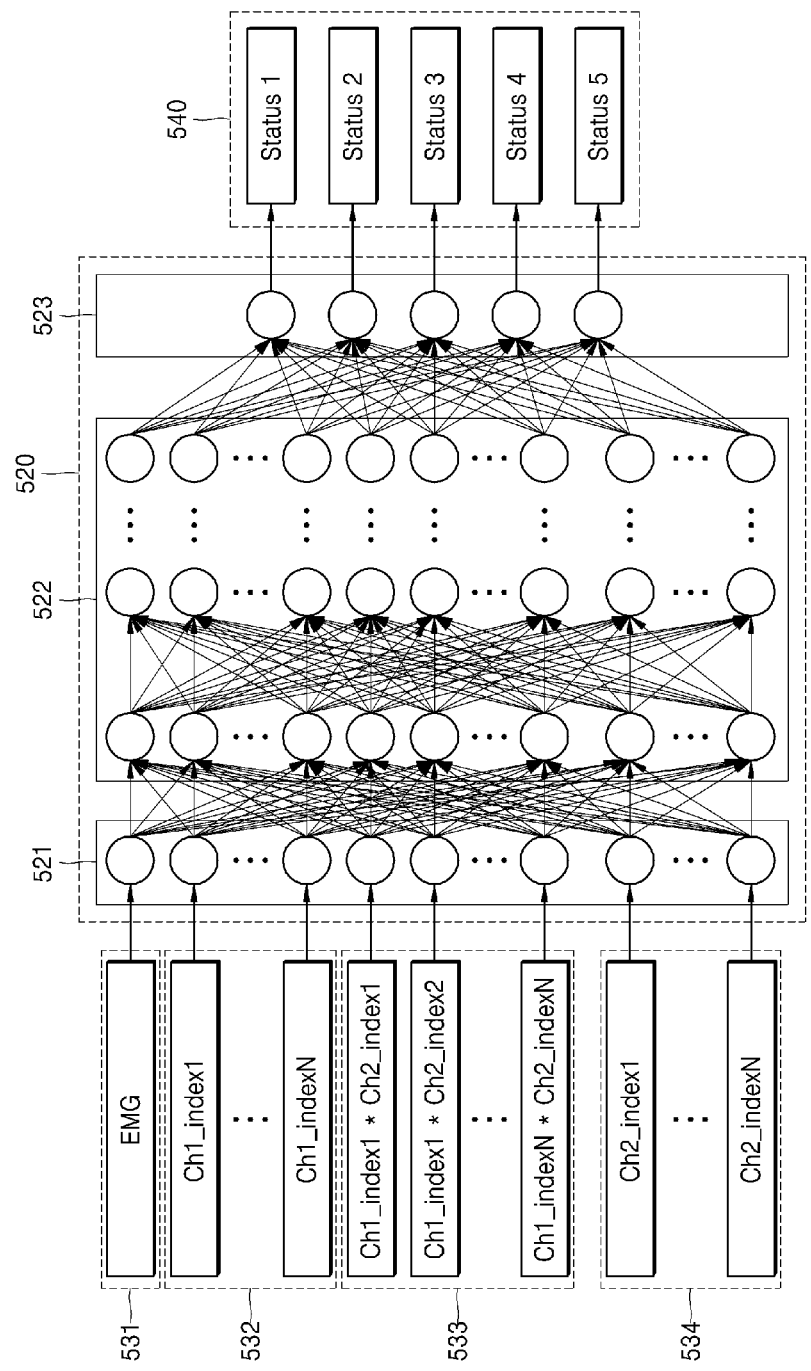
FIG. 8 is a view for describing input data 531, 532, 533, and 534 of an artificial neural network 520 according to an embodiment of the present disclosure and patient status data 540 as output data according to the input data.

FIG. 8 is a view for describing input data 531, 532, 533, and 534 of an artificial neural network 520 according to an embodiment of the present disclosure and patient status data 540 as output data according to the input data.

The controller 120 according to an embodiment of the present disclosure may generate input data 531, 532, 533, and 534 of the artificial neural network 520 in order to calculate a probability value that the patient 300 belongs to each of one or more patient statuses using the artificial neural network 520 that has been trained according to the above-described processes. In this case, the artificial neural network 520 may include an input layer 521 including at least one input node to which input data 531, 532, 533, and 534 are input, an intermediate layer (or a hidden layer) 522 including a plurality of intermediate nodes (or hidden nodes), and an output layer 523 including at least one output node. The intermediate layer 522 may include one or more layers that are fully connected as illustrated in the drawing. When the intermediate layer 522 includes a plurality of layers, the artificial neural network 520 may include a function defining a relationship between respective hidden layers.

Hereinafter, for convenience of description, it is assumed that the controller 120 has calculated first indices for each of N frequency bands from a first section of a first EEG of a patient 300, which have been acquired through the first channel according to the processes described with reference FIGS. 2 to 5, and that the controller 120 has calculated first indices for each of N frequency bands from a first section of a second EEG of the patient 300 acquired through the second channel in the same processes.

Under the above-described assumption, the controller 120 according to an embodiment of the present disclosure may generate $N^2$ pieces of first input data 533 based on a combination of N first indices for the first channel and N first indices for the second channel. The first input data 533 may be an item corresponding to the data 511D of FIG. 7 among the training data for training the artificial neural network 520.

For example, the controller 120 may generate the first input data 533 such that data obtained by multiplying the first index for the first channel and each of N indices for the second channel, and data obtained by multiplying the second index of the first channel and each of N indices for the second channel are included in the first input data 533. Of course, the controller 120 may generate the first input data 533 by applying the same method as described above to each of the remaining indices for the first channel.

The controller 120 according to an embodiment of the present disclosure may generate N pieces of second input data 532 corresponding to the N first indices for the first channel. The second input data 532 may be an item corresponding to the data 511A of FIG. 7 among the training data for training the artificial neural network 520. For example, the controller 120 may generate N pieces of second input data 532 such that the N first indices and the N pieces of second input data 532 for the first channel have the same values, respectively.

The controller 120 according to an embodiment of the present disclosure may generate N pieces of third input data 534 corresponding to the N first indices for the second channel. The third input data 534 may be an item corresponding to the data 511B of FIG. 7 among the training data for training the artificial neural network 520. For example, the controller 120 may generate N pieces of third input data 534 such that the N first indices and the N pieces of third input data 534 for the second channel have the same values, respectively.

The controller 120 according to an embodiment of the present disclosure may generate M pieces of fourth input data 531 based on an EMG signal. The fourth input data 531 may be an item corresponding to the data 511C of FIG. 7 among the training data for training the artificial neural network 520. For example, the controller 120 according to an embodiment of the present disclosure may generate the fourth input data 531 using third indices generated according to the above-described processes.

In an embodiment of the present disclosure, N may be 6, and M may be 1. Therefore, the first input data 533 may include 36 pieces of data, each of the second input data 532 and the third input data 534 may include 6 pieces of data, and the fourth input data 531 may include one piece of data. However, the quantity of data included in each of the data 531 to 534 is illustrative, and the spirit of the present disclosure is not limited thereto.

The controller 120 according to an embodiment of the present disclosure may acquire patient status data 540 including a probability value that the patient 300 belongs to each of one or more of patient statuses by inputting the input data 531, 532, 533, and 534 generated according to the above-described processes to the artificial neural network 520.

The patient status data 540 according to an embodiment of the present disclosure may include a probability value that the patient 300 correspond to each of K patient statuses (K is a natural number). For example, K is 5, and the one or more patient statuses may include an awake status (Status 1), a sedation status (Status 2), a general anesthesia status (Status 3), a hyper or deep anesthesia status (Status 4), and a brain death status (Status 5).

For example, the controller 120 may acquire patient status data 540 such as [0.81, 0.62, 0.34, 0.17, and 0.01] from the artificial neural network 520. This patient status data 540 may mean that the probability that the patient 300 is in the awake status is 81%, the probability that the patient 300 is in the sedation status is 62%, the probability that the patient 300 is in the general anesthesia state is 34%, the probability that the patient 300 is in the hyper or deep anesthesia is 17%, and the probability that the patient 300 is in the brain death status is 1%.

In another embodiment of the present disclosure, each of the K statuses and/or numbers may be variously set. For example, when the present disclosure is used to determine a patient's emotional status or the like, each of the K statuses may be statuses representing the patient's emotion. However, this is illustrative, and the spirit of the present disclosure is not limited thereto.

The controller 120 according to an embodiment of the present disclosure may determine the depth of anesthesia of the patient 300 based on the probability value for each of one or more patient statuses.

More specifically, the controller 120 according to an embodiment of the present disclosure may calculate a normalized probability value by normalizing the probability value for each of one or more patient statuses included in the patient status data 540. For example, the controller 120 may calculate a normalized probability value for each of one or more patient statuses such that a total sum of probability values for respective patient states becomes 1.

In addition, the controller 120 according to an embodiment of the present disclosure may apply a weight set, which corresponds to the patient status having the largest probability value among the normalized probability values, to the normalized probability value.

Figure 9:
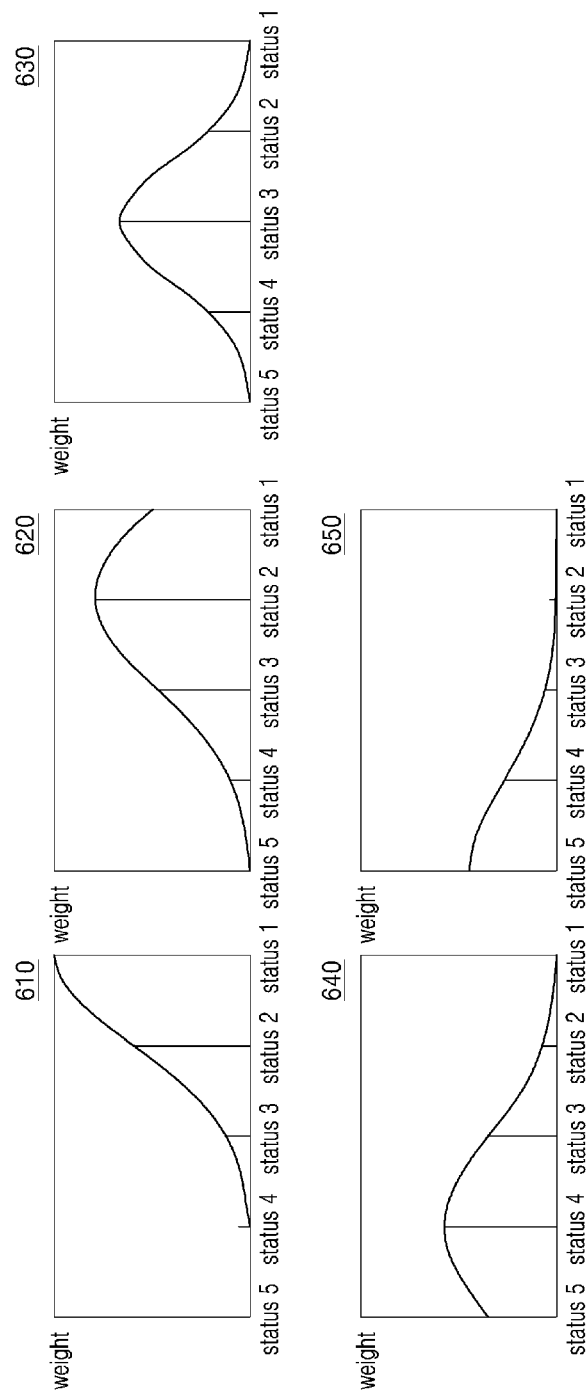
FIG. 9 is a view illustrating one or more exemplary weight sets 610, 620, 630, 640, and 650 in the form of graphs.

FIG. 9 is a view illustrating one or more exemplary weight sets 610, 620, 630, 640, and 650 in the form of graphs. The first weight set 610 is a weight set corresponding to the awake state (Status 1), the second weight set 620 is a weight set corresponding to the sedation status (Status 2), the third weight set 630 is a weight set corresponding to the general anesthesia status (Status 3), the fourth weight set 640 is a weight set corresponding to the hyper or deep anesthesia status (Status 4), and the fifth weight set 650 is a weight set corresponding to the brain death status (Status 5).

For example, when the normalized probability values calculated according to the above-described process are [0.45, 0.25, 0.15, 0.1, and 0.05], the probability that the patient 300 is in the awake state (Status 1) is the highest, and thus the controller 120 may apply the weight set 610 corresponding to the awake status (Status 1) to the normalized probability values, thereby calculating probabilities, such as [0.45, 0.2, 0.5, 0.01, and 0].

The controller 120 according to an embodiment of the present disclosure may determine the depth of anesthesia of the patient 300 based on the sum of normalized probability values to which weights are applied.

In an optional embodiment, the controller 120 according to an embodiment of the present disclosure may determine the final depth of anesthesia of the patient 300 by referring to the depth of anesthesia of the patient 300 determined according to another method.

Figure 10:
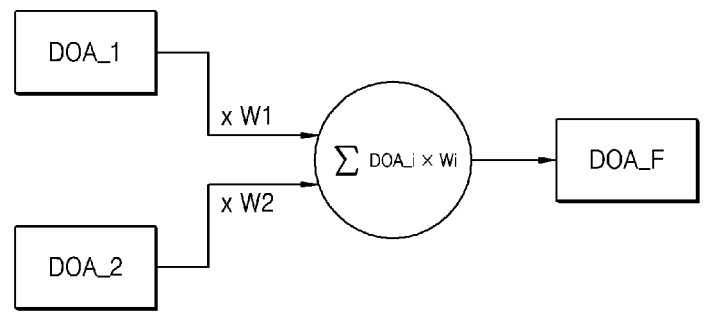
FIG. 10 is a view for describing a process in which the controller 120 determines the final depth of anesthesia of a patient 300 according to a selective embodiment of the present disclosure.

FIG. 10 is a view for describing a process in which the controller 120 determines the final depth of anesthesia of a patient 300 according to a selective embodiment of the present disclosure.

According to an optional embodiment of the present disclosure, the controller 120 may determine the final depth of anesthesia DOA_F of a patient 300 based on the sum of a first depth of anesthesia obtained by applying a predetermined weight W1 to a depth of anesthesia DOA 1 calculated according to the processes described with reference to FIGS. 2 to 9 and a second depth of anesthesia obtained by applying a predetermined weight W2 to a depth of anesthesia DOZ_2 calculated through a second method. In this case, the second method of calculating the depth of anesthesia DOA_2 may be a method of calculating the depth of anesthesia including some processes different from the processes described with reference to FIGS. 2 to 9. For example, the second depth of anesthesia may be a depth of anesthesia determined based on a first index calculated from a patient's EEG, a second index reflecting how much the patient's EEG matches a predetermined pattern, and a third index based on at least one biosignal corresponding to the patient status.

Figure 11:
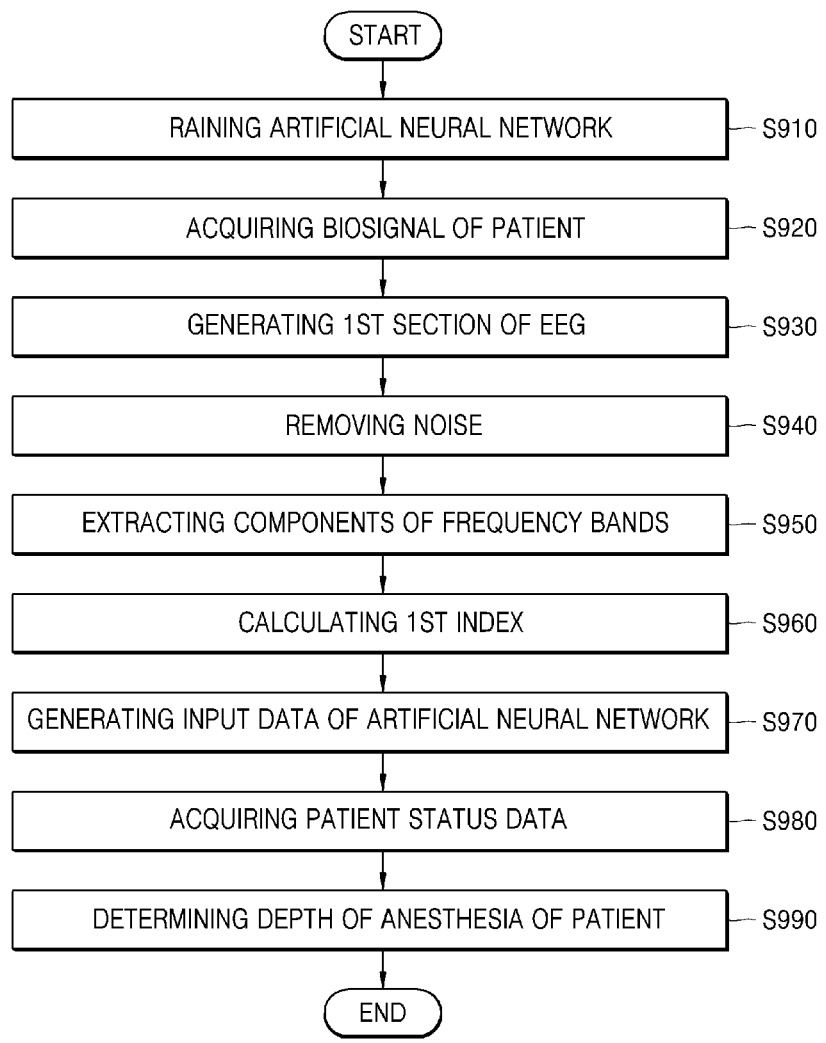
FIG. 11 is a flowchart for describing a consciousness level determination method performed by a user terminal 100 according to an embodiment of the present disclosure.

FIG. 11 is a flowchart for describing a depth of anesthesia measurement method performed by a user terminal 100 according to an embodiment of the present disclosure. Hereinafter, a description overlapping with that made with reference to FIGS. 1 to 10 will be omitted, but FIGS. 1 to 10 will also be referred to in the following description.

The user terminal 100 according to an embodiment of the present disclosure may train an artificial neural network based on multiple pieces of training data (S910).

In the present disclosure, the "artificial neural network" may be a neural network that includes data on which EEG characteristics have been reflected and data on which EMG characteristics have been reflected, and that has learned the correlations between the EEG characteristics, the EMG characteristics and the patient status based on the training data labeled with the patient status data corresponding to the EEG characteristics and the EMG characteristics.

In other words, the artificial neural network may be a neural network that has been trained to output the patient status data in response to input of data on which the EEG characteristic has been reflected and data on which the EMG characteristic has been reflected.

In the present disclosure, the artificial neural network may be implemented as a neural network model of various structures. For example, the artificial neural network may be implemented as a CNN model, an RNN model, or an LSTM model. However, these neural network models are examples, and a means capable of learning the correlation between input and output based on training data can be used as the artificial neural network of the present disclosure.

FIG. 7 is a view for describing a process in which the user terminal 100 according to an embodiment of the present disclosure trains an artificial neural network 520 using multiple pieces of training data 510.

As described above, the artificial neural network 520 may be a neural network that has learned the correlations between the EEG characteristics, the EMG characteristics, and a patient status based on multiple pieces of training data 510.

In this case, each of multiple pieces of training data 510 may include data in which the EEG characteristics have been reflected and data on which the EMG characteristics have been reflected, as described above, and may be data labeled with patient status data corresponding to the EEG characteristics and the EMG characteristics.

For example, first training data 511 may, as data on which EEG characteristics have been reflected include, N pieces of data 511A (N is a natural number) corresponding to first indices for each of N frequency bands calculated from the first section of a first EEG (acquired through the first channel) of a patient 300, N pieces of data 511B corresponding to first indices for each of N frequency bands calculated from the first section of a second EEG (acquired through the second channel) of the patient 300, and $N^2$ pieces of data 511D generated based on a combination of N first indices 511A for the first channel and N first indices 511B for the second channel.

In addition, the first training data 511 may include M pieces of data 511C (M is a natural number) based on an EMG signal, as data on which the EMG characteristics have been reflected.

In addition, the first training data 511 may be labeled with patient state data 511E including a probability that the corresponding patient 300 corresponds to each of K patient statuses. In this case, for example, N may be 6, M may be 1, and K may be 5.

Remaining training data including a second training data 512 and a third training data 513 may also include the same data as the first training data 511, and may be labeled with the same data.

As described above, the present disclosure may train the artificial neural network 520 based on data generated from a patient's biosignals and training data including a probability that the patient corresponds to each of multiple patient statuses. Accordingly, the artificial neural network 520 may output a probability that the corresponding patient corresponds to each of the multiple patient statuses according to the input of data generated from the patient status signals. Hereinafter, it is assumed that the artificial neural network 520 has been trained based on multiple pieces of training data 510 described with reference to FIG. 7.

The user terminal 100 according to an embodiment of the present disclosure may acquire a biosignal of a patient 300 (S920).

The user terminal 100 according to an embodiment of the present disclosure may acquire an EEG of the patient 300. For example, the user terminal 100 may acquire an EEG by receiving the EEG from the signal processor 220 described above. The EEG acquired at this time may be an EEG amplified and sampled at a predetermined sampling frequency. In addition, the user terminal 100 may acquire two EEGs acquired through different channels from the signal processor 220.

Meanwhile, the user terminal 100 according to an embodiment of the present disclosure may further acquire an EMG signal along with an EEG. Of course, the EMG signal acquired at this time may also be an EMG signal amplified and sampled at a predetermined sampling frequency.

The user terminal 100 according to an embodiment of the present disclosure may acquire a biosignal of the patient 300 in real time. In this case, the user terminal 100 may temporarily and/or permanently store the past biosignals in the memory 130 and may use the biosignals for measuring the depth of anesthesia of the patient.

The user terminal 100 according to an embodiment of the present disclosure may generate a first section of an EEG including at least a part of the acquired EEG (S930).

FIG. 2 is a view for describing a method in which the user terminal 100 according to an embodiment of the present disclosure generates a first section of an EEG 400.

Hereinafter, for convenience of description, the EEG 400 of the patient 300 is generated as shown in the drawing, and the current time points are assumed to be 4 seconds, 5 seconds, and 6 seconds, respectively.

In generating the first section of the EEG 400, the user terminal 100 according to an embodiment of the present disclosure may generate a first section to include therein a past EEG within a predetermined time interval from the time point for determining the depth of anesthesia (i.e., the current time point).

For example, when it is assumed that the current time point at which the depth of anesthesia is determined is 4 seconds, the user terminal 100 may generate a first section 410 of a EEG including a past EEG within a predetermined time interval (assumed as 4 seconds) from the current time point (4 seconds). Similarly, when the current time point is 5 seconds, the user terminal 100 may generate a first section 420 of the EEG, and when the current time point is 6 seconds, the user terminal 100 may generate a first section 430 of the EEG.

In this case, the "predetermined time interval" may be variously set depending on system characteristics. For example, in a system requiring a quick response, a predetermined time interval may be set to be relatively short. For example, in a system requiring a correct response, a predetermined time interval may be set to be relatively long.

The user terminal 100 according to an embodiment of the present disclosure may generate the first section for each of two EEGs acquired through different channels according to the above-described processes. In addition, the user terminal 100 according to an embodiment of the present disclosure may repeatedly generate the first section based on the current time point depending on the passage of time (i.e., depending on the change of the time point for determining the depth of anesthesia).

The user terminal 100 according to an embodiment of the present disclosure may remove noise in the first section of the EEG generated according to the above-described processes (S940).

FIG. 3 is a view for describing a method in which the user terminal 100 according to an embodiment of the present disclosure removes noise from the first section 440 of an exemplary EEG and generates a first section 440FLT of the EEG, from which noise has been removed.

The user terminal 100 according to an embodiment of the present disclosure may replace a first partial section 444A having a magnitude exceeding a predetermined threshold magnitude Ath with a second partial section 443A different from the first partial section within the first section 440 of the EEG.

In this case, when the magnitude of the EEG at any one time point within the first partial section 444A exceeds the predetermined threshold magnitude Ath, the user terminal 100 may determine that the magnitude of the EEG within the corresponding section 444A exceeds the predetermined threshold magnitude Ath. In addition, the user terminal 100 may replace the corresponding section 444A using the section 443A adjacent to the section 444A.

Accordingly, the user terminal 100 may generate a first section 440FLT of an EEG, from which noise has been removed, and which has first to third partial sections 441B, 442B, and 443B, which are respectively the same as the first to third partial sections 441A, 442A, and 443A of the first section 440, and a fourth partial section 444B, which is the same as the third partial section 443A of the first section 440.

However, the length and the threshold magnitude Ath of the partial sections, and the method of replacing the partial sections are illustrative, and the spirit of the present disclosure is not limited thereto.

In an optional embodiment, when a pattern, in which the magnitude of the EEG within the first section 440 of the EEG exceeds the predetermined threshold magnitude, corresponds to a preset pattern, the user terminal 100 may replace the first section 440 of the EEG with the second section of the EEG. In this case, the second section of the EEG is a section different from the first section 440 of the EEG, and may be, for example, an EEG of a section adjacent to the first section.

In addition, the "preset pattern" may be variously set depending on the purpose of the system. For example, the preset pattern may be a pattern in which an EEG having a magnitude exceeding a predetermined threshold magnitude is generated in a plurality of partial sections within the same section, or a pattern in which an EEG having a magnitude exceeding a predetermined threshold magnitude is generated in two or more successive partial sections. However, such a pattern is illustrative, and the spirit of the present disclosure is not limited thereto.

The user terminal 100 according to an embodiment of the present disclosure may extract components of one or more frequency bands from the first section of the EEG generated according to the above-described processes (or the first section of an EEG, from which noise has been removed) (S950).

FIG. 4 is a view for describing a process in which the user terminal 100 according to an embodiment of the present disclosure extracts components 411, 412, 413, 414, 415, 416, 417, and 418 of one or more frequency bands from a first section 410FLT of an EEG, from which noise has been removed.

The user terminal 100 according to an embodiment of the present disclosure may extract a first component 412 of 0.5 to 4 Hz, a second component 413 of 4 to 8 Hz, a third component 414 of 8 Hz to 16 Hz, a fourth component 415 of 16 to 25 Hz, a fifth component 416 of 25 to 30 Hz, a sixth component 417 of 30 to 48 Hz, a reference component 411 of 0.5 to 55 Hz, and a BSR component 418 of 0.5 to 30 Hz, from the first section 410FLT of an EEG, from which noise has been removed.

The user terminal 100 according to an embodiment of the present disclosure may extract components 411, 412, 413, 414, 415, 416, 417, and 418 of one or more frequency bands from the first section 410FLT of the EEG, from which noise has been removed using frequency filters that correspond to the one or more frequency bands, respectively. For example, the user terminal 100 may extract the first component 412 using a band-pass filter having a pass band of 0.5 to 4 Hz.

The extracted components 411, 412, 413, 414, 415, 416, 417, and 418 of one or more frequency bands may have the same length of time as the first section 410FLT of the EEG, from which noise has been removed. In addition, the components 411, 412, 413, 414, 415, 416, 417, and 418 of one or more frequency bands may include a magnitude of a component of each frequency band at one or more time points belonging to the first section.

For example, when the sampling frequency of the signal processor 220 is 250 Hz and the length of the first section 410FLT of the EEG, from which noise has been removed, is 4 seconds, 1000 time points (or 1000 sampling time points) and the magnitude of the EEG at each time point may be included within the first section 410FLT of the EEG, from which noise has been removed. Accordingly, the components 411, 412, 413, 414, 415, 416, 417, and 418 of one or more frequency bands may also include the magnitude of the component of each frequency band at each of 1000 time points belonging to the first section.

In other words, the components 411, 412, 413, 414, 415, 416, 417, and 418 of one or more frequency bands may also include the magnitude of the component of each frequency band at each of 1000 time points belonging to the first section.

The user terminal 100 according to an embodiment of the present disclosure may calculate a first index for each of the components 411, 412, 413, 414, 415, 416, 417, and 418 of one or more frequency bands (S960).

FIG. 5 is a view for describing a method in which the user terminal 100 according to an embodiment of the present disclosure calculates a first index. For convenience of description, it is assumed that the graph represented in FIG. 5 relates to a first component, and 15 time points are included in the first section for the first component.

The user terminal 100 according to an embodiment of the present disclosure may calculate a first index based on the extent to which the magnitude of each of the components of one or more frequency bands exceeds a predetermined threshold value Rth with respect to the magnitude of a predetermined reference component in the first section. For example, the user terminal 100 according to an embodiment of the present disclosure may calculate the magnitude of each of the components of one or more frequency bands with respect to the magnitude of the reference component for each of one or more time points (i.e., 15 time points) belonging to the first section.

In this case, the reference component may be the reference component 411 extracted according to the process described with reference to FIG. 4, and the components of one or more frequency bands may be the components 412 to 417 extracted according to the process described with reference to FIG. 4. For example, the user terminal 100 may calculate the ratio R1 of the magnitude of the first component 412 at the first time point of the first section to the magnitude of the reference component 411 at the first time point of the first section. Similarly, the controller may calculate the ratios (R2 to R15) of the magnitude of the first component 412 to the magnitudes of the reference component 411 at the remaining time points. Of course, the user terminal 100 may calculate the ratio at each of the plurality of time points according to the above-described process for each of the remaining components 413 to 417.

The user terminal 100 according to an embodiment of the present disclosure may determine a time point at which the magnitude of the calculated ratio exceeds a predetermined threshold value Rth, as an excess time point. For example, the user terminal 100 may determine a time point corresponding to each of R4, R12, R13, and R14 of FIG. 5 as an excess time point. Of course, the controller may determine the excess time points for the remaining components 413 to 417 according to the same process.

The user terminal 100 according to an embodiment of the present disclosure may calculate a first index based on a ratio of the number of excess points to the total number of time points belonging to the first section. For example, for the first component 412, the user terminal 100 may calculate the first index as 4/15 using 15 that is the total number of time points and 4 that is the number of excess time points. In this case, the user terminal 100 may normalize the first index by multiplying a predetermined value by the calculated first index. Of course, the controller may calculate the first index for each of the remaining components 413 to 417 according to the same process.

Meanwhile, the user terminal 100 according to an embodiment of the present disclosure may determine a predetermined threshold value Rth based on the absolute magnitude of the reference component within the first section. Since the reference component is extracted from a wide frequency band, when the magnitude of the EEG in the first section is large, the predetermined threshold value Rth may be determined relatively high, and when the magnitude of the EEG is small, the predetermined threshold value Rth may be determined relatively low.

The user terminal 100 according to an embodiment of the present disclosure may calculate the first index for each of two EEGs acquired through different channels according to the above-described processes. In addition, the user terminal 100 according to an embodiment of the present disclosure may repeatedly calculate the first indexes for the updated first section according to the update of the first section.

The user terminal 100 according to an embodiment of the present disclosure may generate input data 531, 532, 533, and 534 of the artificial neural network 520 in order to calculate a probability value that the patient 300 belongs to each of one or more patient statuses using the artificial neural network 520 that has been trained according to the above-described processes (S970).

FIG. 8 is a view for describing input data 531, 532, 533, and 534 of an artificial neural network 520 according to an embodiment of the present disclosure and patient status data 540 as output data according to the input data.

Hereinafter, for convenience of description, it is assumed that the user terminal 100 has calculated first indices for each of N frequency bands from a first section of a first EEG of a patient 300, which have been acquired through the first channel according to the processes described with reference FIGS. 2 to 5, and that the user terminal 100 has calculated second indices for each of N frequency bands from a first section of a second EEG of the patient 300 acquired through the second channel in the same processes.

Under the above-described assumption, the user terminal 100 according to an embodiment of the present disclosure may generate $N^2$ pieces of first input data 533 based on a combination of N first indices for the first channel and N first indices for the second channel. The first input data 533 may be an item corresponding to the data 511D of FIG. 7 among the training data for training the artificial neural network 520.

For example, the user terminal 100 may generate the first input data 533 such that data obtained by multiplying the first index for the first channel and each of N indices for the second channel, and data obtained by multiplying the second index of the first channel and each of N indices for the second channel are included in the first input data 533. Of course, the user terminal 100 may generate the first input data 533 by applying the same method as described above to each of the remaining indices for the first channel.

The user terminal 100 according to an embodiment of the present disclosure may generate N pieces of second input data 532 corresponding to the N first indices for the first channel. The second input data 532 may be an item corresponding to the data 511A of FIG. 7 among the training data for training the artificial neural network 520. For example, the user terminal 100 may generate N pieces of second input data 532 such that the N first indices and the N pieces of second input data 532 for the first channel have the same values, respectively.

The user terminal 100 according to an embodiment of the present disclosure may generate N pieces of third input data 534 corresponding to the N first indices for the second channel. The third input data 534 may be an item corresponding to the data 511B of FIG. 7 among the training data for training the artificial neural network 520. For example, the user terminal 100 may generate N pieces of third input data 534 such that the N first indices and the N pieces of the third input data 534 for the second channel have the same values, respectively.

The user terminal 100 according to an embodiment of the present disclosure may generate M pieces of fourth input data 531 based on an EMG signal. The fourth input data 531 may be an item corresponding to the data 511C of FIG. 7 among the training data for training the artificial neural network 520. For example, the user terminal 100 according to an embodiment of the present disclosure may generate the fourth input data 531 using third indices generated according to the above-described processes.

In an embodiment of the present disclosure, N may be 6, and M may be 1. Therefore, the first input data 533 may include 36 pieces of data, each of the second input data 532 and the third input data 534 may include 6 pieces of data, and the fourth input data 531 may include one piece of data. However, the quantity of data included in each of the data 531 to 534 is illustrative, and the spirit of the present disclosure is not limited thereto.

The user terminal 100 according to an embodiment of the present disclosure may acquire patient status data including a probability value that the patient 300 belongs to each of one or more patient statuses by inputting the input data 531, 532, 533, and 534 generated according to the above-described processes to the artificial neural network 520 (S980).

The patient status data 540 according to an embodiment of the present disclosure may include a probability value that the patient 300 correspond to each of K patient statuses (K is a natural number).

For example, K is 5, and the one or more patient statuses may include an awake status (Status 1), a sedation status (Status 2), a general anesthesia status (Status 3), a hyper or deep anesthesia status (Status 4), and a brain death status (Status 5).

For example, the user terminal 100 may acquire patient status data 540 such as [0.81, 0.62, 0.34, 0.17, and 0.01] from the artificial neural network 520. This patient status data 540 may mean that the probability that the patient 300 is in the awake status is 81%, the probability that the patient 300 is in the sedation status is 62%, the probability that the patient 300 is in the general anesthesia state is 34%, the probability that the patient 300 is in the hyper or deep anesthesia is 17%, and the probability that the patient 300 is in the brain death status is 1%.

In another embodiment of the present disclosure, each of the K statuses and/or numbers may be variously set. For example, when the present disclosure is used to determine a patient's emotional status or the like, each of the K statuses may be statuses representing the patient's emotion. However, this is illustrative, and the spirit of the present disclosure is not limited thereto.

The user terminal 100 according to an embodiment of the present disclosure may determine the depth of anesthesia of the patient 300 based on the probability value for each of one or more patient statuses (S990).

More specifically, the user terminal 100 according to an embodiment of the present disclosure may calculate a normalized probability value by normalizing the probability value for each of one or more patient statuses included in the patient status data 540. For example, the user terminal 100 may calculate a normalized probability value for each of one or more patient statuses such that a total sum of probability values for respective patient states becomes 1.

In addition, the user terminal 100 according to an embodiment of the present disclosure may apply a weight set, which corresponds to the patient status having the largest probability value among the normalized probability values, to the normalized probability value.

FIG. 9 is a view illustrating one or more exemplary weight sets 610, 620, 630, 640, and 650 in the form of graphs. The first weight set 610 is a weight set corresponding to the awake state (Status 1), the second weight set 620 is a weight set corresponding to the sedation status (Status 2), the third weight set 630 is a weight set corresponding to the general anesthesia status (Status 3), the fourth weight set 640 is a weight set corresponding to the hyper or deep anesthesia status (Status 4), and the fifth weight set 650 is the brain death status (Status 5).

For example, when the normalized probability values calculated according to the above-described process are [0.45, 0.25, 0.15, 0.1, and 0.05], the probability that the patient 300 is in the awake state (Status 1) is the highest, and thus the user terminal 100 may apply the weight set 610 corresponding to the awake status (Status 1) to the normalized probability values, thereby calculating probabilities, such as [0.45, 0.2, 0.5, 0.01, and 0].

The user terminal 100 according to an embodiment of the present disclosure may determine the depth of anesthesia of the patient 300 based on the sum of normalized probability values to which weights are applied.

In an optional embodiment, the user terminal 100 according to an embodiment of the present disclosure may determine the final depth of anesthesia of the patient 300 by referring to the depth of anesthesia of the patient 300 determined according to another method.

FIG. 10 is a view for describing a process in which the user terminal 100 determines the final depth of anesthesia of a patient 300 according to a selective embodiment of the present disclosure.

According to an optional embodiment of the present disclosure, the user terminal 100 may determine the final depth of anesthesia DOA_F of a patient 300 based on the sum of a first depth of anesthesia obtained by applying a predetermined weight W1 to a depth of anesthesia DOA 1 calculated according to the processes described with reference to FIGS. 2 to 9 and a second depth of anesthesia obtained by applying a predetermined weight W2 to a second depth of anesthesia DOZ_2 calculated through a second method. In this case, the second method of calculating the depth of anesthesia DOA_2 may be a method of calculating the depth of anesthesia including some processes different from the processes described with reference to FIGS. 2 to 9. For example, the second depth of anesthesia may be a depth of anesthesia determined based on a first index calculated from a patient's EEG, a second index reflecting how much the patient's EEG matches a predetermined pattern, and a third index based on at least one biosignal corresponding to the patient status.

The embodiments of the present disclosure described above may be implemented through computer programs executable through various components on a computer, and such computer programs may be recorded in computer-readable media. In this case, the media may store a program executable by a computer. As examples of the media, there may be a magnetic medium such as a hard disc, a floppy disc, or a magnetic tape, an optical recording medium such as a CD-ROM or a DVD, a magneto-optical medium such as a floptical disc, and media configured to store program instructions, including, for example, a ROM, a RAM, and a flash memory.

Meanwhile, the computer programs may be those specially designed and constructed for the purposes of the present disclosure or they may be of the kind well known and available to those skilled in the computer software arts. Examples of computer programs may include not only machine-language code created by a compiler, but also high-level language code executable by a computer using an interpreter or the like.

Specific execution modes described herein are represented as embodiments of the present disclosure, and are not intended to limit the scope of the present disclosure in any way. For brevity of description, descriptions of conventional electronic configurations, control systems, software, and other functional aspects of such systems may be omitted. In addition, the connections or connection members corresponding to the lines between the components illustrated in the drawings are illustrative examples of functional connections and/or physical or circuit connections. In an actual device, the connections or connection members may appear as alternative or additional various functional connections, physical connections, or circuit connections. When there is no specific wording such as "essentially" or "critically" with respect to a component, the component may not be a necessary component for application of the present disclosure.

Therefore, the spirit of the present disclosure should not be limited to the above-described embodiments, and it is intended that not only the appended claims, but also all ranges equivalent to or equivalently changed from the claims should be considered to fall within the spirit of the present disclosure.

What is claimed is:

1. A method for determining a consciousness level of a patient, the method comprising:
    a step of extracting components of one or more frequency bands from a first section of an EEG;
    a step of calculating a first index for each of the components of one or more frequency bands, wherein the first index is calculated based on a degree to which a magnitude of each of the components of one or more frequency bands with respect to a magnitude of a predetermined reference component in the first section exceeds a predetermined threshold value;
    a step of calculating a probability value of each of one or more patient statuses from the first index for each of the components of one or more frequency bands using a trained artificial neural network; and
    a step of determining the consciousness level of the patient based on the probability value of each of the one or more calculated patient statuses,
    wherein the components of one or more frequency bands include a magnitude of a component of each of the frequency bands at one or more time point belonging to the first section, and
    wherein the step of calculating the first index comprises:
        a step of calculating the magnitudes of the components of one or more frequency bands with respect to a magnitude of the reference component for each of the one or more time points;
        a step of determining a time point at which the calculated magnitudes exceed the predetermined threshold value as an excess time point; and
        a step of calculating the first index based on a ratio of a number of excess time points to a total number of time points belonging to the first section.

2. The method of claim 1, wherein, before the step of extracting the components of one or more frequency bands, the method further comprises:
    a step of acquiring the patient's EEG;
    a step of generating the first section of the EEG including at least a part of the acquired EEG; and
    a step of removing noise from the first section of the EEG, and
    wherein, in the step of extracting the components of one or more frequency bands, the components of one or more frequency bands are extracted from the first section of the EEG, from which the noise has been removed.

3. The method of claim 2, wherein, in the step of acquiring the EEG, the EEG of the patent sampled at a predetermined sampling frequency is acquired.

4. The method of claim 2, wherein, in the step of generating the first section of the EEG, the first section of the EEG is generated such that the EEG within a predetermined time interval from a time point of determining the consciousness level is included therein.

5. The method of claim 2, wherein, the step of removing the noise comprises:
    a step of replacing a first partial section including a time point at which the magnitude of the EEG exceeds a predetermined threshold magnitude within the first section of the EEG with a second partial section different from the first partial section, and
    wherein the first partial section and the second partial section are at least a part of the first section.

6. The method of claim 2, wherein the step of removing the noise comprises:
    a step of replacing the first section of the EEG with a second section of the EEG when a pattern, in which the magnitude of the EEG within the first section of the EEG exceeds the predetermined threshold magnitude, corresponds to a preset pattern,
    wherein the second section is different from the first section and is at least a part of the EEG.

7. The method of claim 1, wherein, in the step of extracting, a first component of 0.5 to 4 Hz, a second component of 4 to 8 Hz, a third component of 8 Hz to 16 Hz, a fourth component of 16 to 25 Hz, a fifth component of 25 to 30 Hz, a sixth component of 30 to 48 Hz, and a reference component of 0.5 to 55 Hz are extracted from the first section of the EEG.

8. The method of claim 1, wherein the predetermined threshold value is determined based on an absolute magnitude of the reference component within the first section.

9. The method of claim 1, wherein, before the step of calculating the probability value, the method further comprises:
    a step of generating input data of the artificial neural network using a combination of first indices for each of the components of one or more frequency bands.

10. The method of claim 9, wherein a first index for each of N frequency bands (N is a natural number) is calculated from the first section of a first EEG of the patient acquired through a first channel, and a first index for each of the N frequency bands is calculated from a first section of a second EEG of the patient acquired through a second channel distinguished from the first channel, and
    wherein the step of generating the input data comprises:
        a step of generating $N^2$ pieces of first input data based on a combination of the N first indices for the first channel and the N second indices for the second channel;
        a step of generating N pieces of second input data corresponding to the N first indices for the first channel;
        a step of generating N pieces of third input data corresponding to the N first indices for the second channel;

a step of generating M pieces of fourth input data (M is a natural number) based on an EMG signal; and a step of generating the input data including the first input data, the second input data, the third input data, and the fourth input data.

11. The method of claim 10, wherein the N is 6, and the M is 1.

12. The method of claim 1, wherein the artificial neural network is a neural network that includes data on which an EEG characteristic has been reflected and data on which an EMG characteristic has been reflected, and that has learned correlations between the EEG characteristic, the EMG characteristic, and the patient status based on training data labeled with the patient status data corresponding to the EEG characteristic and the EMG characteristic, wherein the data on which the EEG characteristic has been reflected comprises:

$N^2$ pieces of first data based on a combination of N first indices (N is a natural number) for an EEG acquired through a first channel and N first indices for an EEG acquired through the second channel;

N pieces of second data corresponding to the N first indices for the first channel;

N pieces of third data corresponding to the N first indices for the second channel; and M pieces of fourth data (M is a natural number) based on the EMG signal, wherein the patient status data includes a probability that the patient corresponds to each of K patient statuses (K is a natural number).

13. The method of claim 1, wherein the step of determining the consciousness level comprises:

a step of calculating a normalized probability value by normalizing a probability value of each of the one or more patient statuses;

a step of applying a weight set corresponding to a patient status having a largest probability value among normalized probability values to the normalized probability values; and a step of determining the consciousness level based on a sum of weighted normalized probability values.

14. The method of claim 13, wherein the one or more patient statuses comprises an awake status, a sedation status, a general anesthesia status, a deep anesthesia status, and a brain death status, and wherein, in the step of applying the weight set, any one of weight sets for each of the five patient statuses is applied to the normalized probability values.

15. The method of claim 13, wherein, in the step of determining the consciousness level based on the sum of the weighted normalized probability values, the consciousness level is determined based on a first consciousness level obtained by applying a predetermined first weight to the sum of the weighted normalized probability values and a consciousness level obtained by applying a second weight value to a second consciousness level determined through a second method.

16. A non-transitory computer-readable storage medium storing a program that, when executed using a computer, causes the method of claim 1 to be performed.

* * * * *